United States Patent [19]
Carlotti et al.

[11] Patent Number: 5,955,267
[45] Date of Patent: Sep. 21, 1999

[54] PROBE AND METHOD FOR DETECTING YEAST OF SPECIES *CANDIDA KRUSEI*

[75] Inventors: Arnaud Carlotti, Lyons; Jean Villard, Saint Romain Au Mont D'Or, both of France

[73] Assignee: Bio Merieux S.A., Marcy l'Etoile, France

[21] Appl. No.: 08/632,442

[22] PCT Filed: Sep. 7, 1993

[86] PCT No.: PCT/GB94/01931

§ 371 Date: Jun. 25, 1996

§ 102(e) Date: Jun. 25, 1996

[87] PCT Pub. No.: WO95/11991

PCT Pub. Date: May 4, 1995

[30] Foreign Application Priority Data

Oct. 27, 1993 [FR] France .................................. 93 13035

[51] Int. Cl.⁶ .............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search ............................... 435/6; 536/23.1, 536/24.3; 935/76, 77, 78

[56] References Cited

U.S. PATENT DOCUMENTS

| | | | |
|---|---|---|---|
| 5,426,026 | 6/1995 | Jordan .......................................... | 435/6 |
| 5,426,027 | 6/1995 | Lott et al. .................................... | 435/6 |
| 5,635,353 | 6/1997 | Lott et al. .................................... | 435/6 |
| 5,707,802 | 1/1998 | Sandhu et al. ............................... | 435/6 |

FOREIGN PATENT DOCUMENTS

| | | | |
|---|---|---|---|
| 0 335 633 A3 | 11/1989 | European Pat. Off. .......... | C12Q 1/68 |
| 0 422 869 A2 | 4/1991 | European Pat. Off. .......... | C12Q 1/68 |
| WO9005195 | 5/1990 | WIPO .............................. | C12Q 1/68 |

OTHER PUBLICATIONS

Carlotti et al., Current Genetics 31: 255–263 (1997).
Soll et al., J. Clinical Microbiology 26(8) : 1448–1459 (1988).
Carlotti et al., J. Clinical Microbiology 32(7) : 1691–1699 (Jul. 1994).
Wickes et al., J. General Microbiology 138: 901–907 (1992).
Niesters et al., J. Clinical Microbiology 31(4) : 904–910 (Apr. 1993).
Sullivan et al., J Clinical Microbiology 31(8) : 2124–2133 (Aug. 1993).
Burgener–Kairuz et al., J Clinical Microbiology 32(8) : 1902–1907 (Aug. 1994).

*Primary Examiner*—W. Gary Jones
*Assistant Examiner*—Ethan Whisenant
*Attorney, Agent, or Firm*—Bacon & Thomas

[57] ABSTRACT

The detection and characterization of yeasts belonging to the species *Candida krusei* is disclosed. A specific probe, in particular a DNA probe for detecting and, in particular, identifying the species *Candida krusei* and typing (infraspecific characterization) *Candida krusei* strains, is particularly disclosed. The expected results are achieved by means of a probe selected from the following genetic (or related) tools:

- at least one portion of at least one DNA and/or RNA fragment (F) with a size of 7-4 kb, said fragment being specifically hybridizable with the DNA and/or RNA of *Candida krusei* while not coding for rRNA;
- at least one portion of the transcription and/or translation products of (F);
- and a combination of the abovementioned tools.

The probe may be used in medical diagnostics and industrial therapeutical tests.

22 Claims, 2 Drawing Sheets

PROBE AND METHOD FOR DETECTING YEAST OF SPECIES *CANDIDA KRUSEI*

TECHNICAL FIELD

The present invention relates to the detection and characterization of yeasts belonging to the species *Candida krusei*. In particular, it provides a specific probe, especially a nucleic acid probe, for the detection and particularly identification of the species *Candida krusei* and for the typing (infrapecific characterization) of strains of the species *Candida krusei*.

PRIOR ART

Yeasts are fungi, i.e. eukaryotic microorganisms, in which the unicellular form is predominant (Barnett J. W., R. W. Payne and D. Yarrow, Yeasts: characteristics and identification, 2nd Edition, Cambridge University Press, Cambridge, 1991).

The genus Candida is a heterogeneous genus which groups together anamorphous species, i.e. species whose mode of sexual reproduction is or was unknown. When this mode of sexual reproduction is discovered, the species are generally reclassified within an already described species (teleomorph). Thus *Issatchenkia orientalis* is the teleomorph of *Candida krusei*.

In the taxonomy of yeasts, it is therefore possible to encounter two different species names for describing one and the same taxon (group) of yeasts.

In normal practice, the species name *Candida krusei* is the most commonly used and it is the one which will be employed indiscriminately in the present disclosure to denote *Candida krusei* or *Issatchenkia orientalis*.

*Candida krusei* is one of the ten principal species of yeasts of the genus Candida which are responsible for infections in humans or animals. This species is sometimes responsible for the degradation of food products. It is also used for certain industrial biotransformations.

*Candida krusei* infections are called "*C. krusei* candidoses" or "*C. krusei* mycoses"; they can affect practically any tissues in the human body. Systemic, generalized or deep infections are the most serious and can be fatal. The mortality rate can be high.

Yeasts of the species *Candida krusei* are opportunist and ubiquitous; their prevalence and pathogenicity are high in immunosuppressed subjects, especially in patients suffering from neutropenia, AIDS, cancer etc., who are particularly sensitive to *C. krusei* infections.

Finally, *C. krusei* candidoses are obviously very contagious in the same way as any other fungal diseases.

The whole difficulty of treating infections of this type arises from the fact that strains of *Candida krusei* are relatively resistant to certain antifungal agents and to fluconazole in particular. What is even more troublesome, however, is that the use of these antifungal agents in prophylaxis, or even in therapy, would favor colonization of the subjects by endogenous strains if they were present in the patient.

Consequently, rapid detection and precise and reliable identification, as well as typing of the strains of this species, are increasingly necessary, especially for enabling an appropriate antifungal treatment to be applied. Moreover, there is a real need for reliable epidermiological markers for use in epidermiological studies or for tracing stains in the agrifoodstuffs or fermentation industries.

One is forced to note, however, that the conventional methods of identifying yeasts are not entirely satisfactory in all these respects.

Thus, known methods include especially those described by Barnett, J. W., R. W. Payne and D. Yarrow in: "Yeasts: characteristics and identification", 2nd edition, Cambridge University Press, Cambridge, 1991, which require prior isolation of the microorganism in pure culture and then a study of its morphological and especially physiological characteristics (more than 80 tests), these ions together taking from 10 to 30 days for one identification. These methods are therefore tedious and particularly long. They are restricted to reference laboratories and cannot be used in normal practice.

Although more rapid and more rational, the miniaturized and standardized methods of identifying yeasts of medical importance still include prior isolation and then identification of the microorganism by meals of physiological tests, which are performed for example by using API® strips. Such tests take about 5 to 7 days to achieve an identification. Furthermore, these techniques do not always enable the species *Candida krusei* to be identified unambiguously, there being possible or even frequent confusions with species such as *Candida glabrata, Candida inconspicua, Candida lipolytica, Candida norvegensis, Candida rugosa* and *Candida valida*.

With the advances in molecular biology, a new technology utilizing the principle of DNA-DNA or DNA-RNA hybridization has been developed for perfecting rapid, sensitive and specific identification tests. The genetic material of the microorganisms present in the sample is detected directly with the aid of labeled DNA or RNA probes. Detection and identification can be carried out simultaneously without prior isolation.

The rare methods described for identifying *Candida krusei* with the aid of nucleic acid probes have the disadvantage of being based on very small probes (30 to 35 nucleotides); these require the use of radioactive labeling, which is more sensitive than non-radioactive labeling but is also more restrictive.

Another disadvantage of these probes associated with their small size is expressed in the context of their use in polymerization chain techniques (PCR). These consist in amplifying a given DNA sequence by multiplying it from a pair of double-stranded primers using a polymerase. Such amplifications can be employed for diagnostic purposes in order to facilitate detection. As these probes would be used as primers in PCR, the possible choices of primers would be limited to a small sequence of 30 to 35 nucleotides.

These probes are generally directed against target DNA sequences coding for the small subunits 5S or 18S of ribosomal RNA (ssu rRNA). These targets are conventionally chosen because the DNA sequences coding for the ribosomal RNAs are the first to have been determined. There is a problem associated with the choice of sequences coding for ssu rRNAs as targets. In fact, these sequences have a universal character, i.e. a large number of them are found in all microorganisms (yeasts, fungi, bacteria); they are said to be "hyperconserved".

In addition, ssu rRNAs are present in large amounts in cells, the result of which is to increase the sensitivity of identification methods based on its detection.

It follows that for these two reasons at least, they can be the cause of false positives in both PCR and detection.

Moreover, none of the probes described in the prior art permits the typing of strains, i.e. differentiation between the individuals within the species, these individuals being assigned to only one group: the species *Candida krusei*. In fact, the previously described probes do not permit typing of the strains of C. krusei because they do not reveal sufficient polymorphism in the size of the restriction fragments among the strains of this species Candida krusei, so they do not constitute a reliable epidermiological marker.

The following may be mentioned as illustrations of such known probes which imperfectly meet the technical needs existing in the art:

the oligonucleotide probes developed by Gene-Trak Systems and directed against sequences of 30 nucleotides (probe 1351), 33 nucleotides (probe 1537) and 35 nucleotides (probe 1530) of the DNA coding for 18S ribosomal RNA. These probes are described in European patent application no. 0 422 869. They were tested against 4 strains of Candida krusei. It should be noted that the Examples in said patent application do not refer to the detection of Candida krusei by hybridization in specimens of human blood, sputum or cerebrospinal fluid. Furthermore, these probes do not make it possible to differentiate between strains within the species Candida krusei;

the probe described by Niesters and coworkers (Niesters et al., 1993, Rapid, polymerase chain reaction-based identification assays for Candida species. J. Clin. Microbiol., 31, 904–910, 1993). This is a probe of 20 nucleotides (oligonucleotide 705) which is directed against a specific sequence of the amplification product of the small subunit of ribosomal RNA (ssu rRNA). This study is utilized in a method of identifying the species of the genus Candida, said method being based on the chain amplification (PCR) of sequences of the gene coding for the ssu rRNA, followed by direct sequencing of these sequences. Once again, this methodology involves the ribosomal RNA. It has the disadvantage of requiring direct sequencing of the amplification product, a technique accessible to only a limited number of research laboratories and certainly not applicable to routine work. Furthermore, according to the authors, oligonucleotide 705 does not permit specific amplification of the DNA of Candida krusei, nor do the probes described by Niesters and coworkers make it possible to type strains of Candida krusei.

BRIEF DESCRIPTION OF THE INVENTION

In this state of the art, one of the essential objects of the present invention is to provide a perfectly specific probe for detecting yeasts of the species Candida krusei.

A further object of the invention is to provide a probe, especially a nucleic acid probe, of sufficient size to allow the use of a marker other than a radioactive marker, which is therefore more convenient to use.

A further object of the invention is that this nucleic acid probe be directed against target sequences of DNA other than that coding for small subunits 5S or 18S of ribosomal RNA, which are overall poorly representative of the species because they are very highly conserved in microorganisms.

A further object of the invention is that this probe be able to be used in complex biological media of the type comprising human blood, sputum or cerebrospinal fluid.

A further object of the invention is that the Candida krusei probe make it possible to go beyond simple detection and allow precise identification and typing of yeasts within the species Candida krusei.

These and other objects are achieved by the present invention, which relates to a probe for the specific and/or infraspecific detection of yeasts of the species Candida krusei, characterized in that it is selected from the following genetic (or related) tools:

at least part of:
at least one DNA and/or RNA fragment F
    formed by at least one of the two fragments $F_1$ and $F_2$ derived from digestion of the total DNA of the strain LMCK 31 by the restriction enzyme EcoRI,
    with a size of between 7 and 4 kb, said fragment hybridizing specifically with DNA and/or RNA of Candida krusei
    and not coding for the synthesis of ribosomal RNA,
and/or at least one analog Fa of this (or these) fragment(s) F resulting from the degeneracy of the genetic code,
and/or at least one cDNA fragment Fc complementary with the fragment F,
at least part of the transcription products of the abovementioned fragment(s) F and/or Fa and/or Fc,
at least part of the translation products of the abovementioned fragment(s) F and/or Fa and/or Fc,
and a combination of the abovementioned tools.

DETAILED DESCRIPTION OF THE INVENTION:

It is therefore to the credit of the Applicant on the one hand to have been able to isolate at least one nucleic acid fragment F with a substantial size greater than or equal to 4 kb as well as the MRNA and the proteins capable of resulting therefrom, and on the other hand to use these genetic or related tools for the specific identification of yeasts of the species Candida krusei, as well as for their infraspecific characterization.

In a first stage, the research strategy developed by the Applicant initially consisted in selecting a particular strain of Candida krusei, namely the one called LMCK 31 hereafter. This strain originates from a bronchoalveolar specimen taken from a hospitalized patient suffering from a Candida krusei disease.

The strain LMCK 31, which constitutes one of the subjects of the present invention, was deposited in the collection nationale de culture de microorganismes (CNCM) at the Institut Pasteur, PARIS, on Oct. 22, 1993 under the reference I 1372.

In a second stage, the Applicant isolated and characterized the probe, especially nucleic acid probe, according to the invention, which, in a preferred embodiment, consists of at least part of at least one of the two fragments $F_1$ and $F_2$ derived from digestion of the total DNA of the strain LMCK 31 by the restriction enzyme EcoRI. These fragments $F_1$ and $F_2$ are separated by agarose gel electrophoresis, extracted and then cloned by the conventional techniques of molecular biology.

They were selected from the restriction profiles of the total DNA of LMCK 31, among a multitude of other fragments, after much research and experimentation.

The two fragments $F_1$ and $F_2$ are preferably present in the probe in the following relative proportions $F_1/F_2$: 99/1 to 1/99, preferably 80/20 to 20/80 and particularly preferably about 50:50 parts by weight.

At least part of at least one of the two fragments $F_1$ and $F_2$, and preferably both of them in their entirety, are used as a probe according to the principle of DNA-DNA or DNA-RNA hybridization. This probe makes it possible to perform tests for the rapid, sensitive and specific detection and identification of Candida krusei and also constitutes an excellent marker for typing strains of this species, by virtue of its ability to reveal a polymorphism in the size of the restriction fragments of the total DNA of *Candida krusei*. This latter property constitutes one of several novel features of the present invention.

It has to be considered that the hybridization of the nucleic acid probe of the invention with target nucleic acid sequences of *C. krusei* can be effected with the whole of the fragments $F_1$ and $F_2$ referred to above, but can also be effected with only a fraction of these fragments, the size of which preferably remains greater than or equal to 0.1 kb.

According to one particularly advantageous modality of the invention, the probe, in its nucleic acid variant, is characterized in that each fragment $F_1$ and $F_2$ has a size of between 6.6 and 4.4 kb. Even more preferably, $F_1$ and $F_2$ have sizes of about 5.6 and 5.4 kb respectively.

The nucleic acid probe according to the invention is labeled with the aid of labeling means capable of revealing hybridization. These labeling means may or may not be radioactive. Given that this probe has a relatively large size and that the quantity of markers fixed to the probe is proportional to its length, it is therefore possible to fix much more to the probe according to the invention (greater than or equal to 4 kb) than to probes made of smaller nucleotide sequences (less than or equal to 35 bases). This makes it possible to mitigate the well-known fact that the sensitivity of non-radioactive labeling is lower than that of radioactive labeling.

Now, non-radioactive markers are easy to manipulate and are accessible to all laboratories in the medical or agri-foodstuffs sector, in contrast to radioactive markers, the use of which is subject to strict and regulated conditions and is therefore strictly limited to authorized laboratories.

$^{32}P$ may be mentioned among the conventional radioactive markers.

Examples of non-radioactive markers which may be mentioned are fixed enzymes such as peroxidase.

Because of its large size, the probe according to the invention can advantageously be employed as a source of specific primer(s) for use in polymerization chain reactions (PCR).

This (or these) primer(s) constitute a further subject of the invention.

Another feature of these fragments $F_1$ and $F_2$ is that they only pair with the DNA and/or RNA of *Candida krusei* or its perfect form, namely *Issatchenkia orientalis,* and not with that of other yeasts of medical interest, filamentous fungi or bacteria. This specificity is further improved by the fact that these fragments $F_1$ and $F_2$ do not hybridize with a target DNA coding for 18S ribosomal RNA, in contrast to the known nucleic acid probes.

According to another characteristic of the invention, at least one of the fragments $F_1$ and $F_2$ is capable of hybridizing with at least one of the fragments derived from digestion of the total DNA of the *Candida krusei* strain LMCK 31 by the restriction enzyme HinfI, the size of which is between 7.0 and 2.0 kb and preferably between 3.8 and 2.5 kb.

In fact, the probe hybridizes especially with at least one of the four fragments derived from this digestion by HinfI, the respective sizes of which are as follows: about 3.4, 3.5, 3.1 and 2.9 kb.

The sensitivity of this probe is perfectly suited to the detection and/or typing of *Candida krusei* by dot-blot or Southern blot hybridization.

This sensitivity is verified in indirect hybridization assays (deposition, dot-blot or Southern blot method), but also in direct hybridization experiments in situ. The latter consist in making a filter blot of colonies in the growth phase on a solid culture medium and bringing the hybridization probe directly to the filter.

Under these conditions, the nucleic acid probe according to the invention makes it possible to detect a colony of *Candida krusei* among more than 30 colonies of different species after 12 to 24 hours of growth, without prior purification.

The *Candida krusei* probe can be of a nucleic acid nature, i.e. it can consist of nucleic acids of the types comprising DNA, cDNA and mRNA derived from transcription of the DNA, or their variants and analogs.

According to another aspect of the invention, however, the probe can also consist of the translation products of this or these DNAs and/or RNAs, these actually being the proteins which can be synthesized by reading the information coded by the mRNA.

It is interesting to note that the probe according to the invention can be efficiently employed in any complex medium like the following biological media: blood, sputum and cerebrospinal fluid. This does not interfere in any way with its detection properties.

The present invention further relates to a method for the specific detection of yeasts of the species *Candida krusei,* which consists in using at least one nucleic acid probe as described above.

This method comes within the scope of the methodologies known in the field of the genetic detection and identification of microorganisms.

In this method:

the total genomic DNA is extracted from the strains to be studied, this total DNA is optionally subjected to enzymatic digestion by at least one restriction enzyme, the optionally digested, total DNA is denatured, the now denatured, total DNA is brought into contact with the probe, which itself has previously been denatured and provided with at least one marker, in order to effect hybridization, the DNA and the unhybridized probe are removed and the hybridization is revealed with the aid of the marker.

This is a hybridization technique in which the target DNA of the microorganism to be studied is subjected to denaturation, with or without prior enzymatic digestion. The next step is that of recombining the separate stands of denatured DNA with the probe in order to re-form novel base pairings.

During this recombination step, the single-stranded molecules of the probe and target are placed under conditions which are more or less favorable for pairing (more or less stringent). Under very stringent conditions, only the molecules whose sequences are complementary over a large number of bases hybridize to form a double-stranded molecule. The probe is then specific for the target.

In the case of a probe labeled with a radioactive element such as $^{32}P$ or with a grafted enzyme such as peroxidase, for example, the hybridization is easily revealed qualitatively and quantitatively.

It is apparent from the above that the nucleic acid and/or protein probe according to the invention, and the method which applies them, are perfectly specific for *Candida* krusei and offer an excellent sensitivity, which gives them outlets of considerable interest in the applied fields of the identification and screening differentiation between strains of this species (medical diagnostics, industrial controls in foodstuffs, fermentation, etc.). Candida krusei is detected rapidly (24 to 48 hours) and unambiguously. These are yet further economic and industrial assets for the probe and method according to the invention.

In addition to detection, which groups together the identification and typing of microorganisms of the Candida krusei type, the probe according to the invention could be applied in the context of a therapeutic strategy directed against Candida krusei diseases. More precisely, this means that the fragments forming the probe can be employed as a target for active principles against Candida species. This role of a target for drugs could be played by the DNA or its transcription products (MRNA) or translation products (proteins).

The invention will be better understood and other advantages and practical variants thereof will become clearly apparent from the following non-limiting Examples, which describe, with reference to the attached drawings, the constitution of a probe according to the invention, its preparation and several C. krusei detection procedures which apply it.

EXAMPLES

Figure 1:
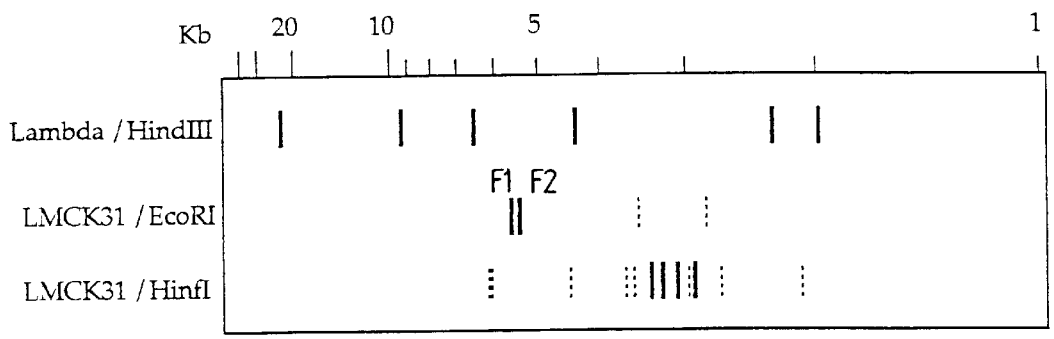
FIG. 1, which shows the results of hybridizing the probe $F_1$, $F_2$ with the EcoRI or HinfI restriction fragments of the total DNA of Candida krusei LMCK 31.

Example 1: Nucleic Acid Probe $R_1$, $F_2$

In the present Example, the probe according to the invention consists of two fragments $F_1$ and $F_2$ derived from digestion of the total DNA of the strain LMCK 31 by EcoRI and having respective sizes of about 5.6 and 5.4 kb. The fragments $F_1$ and $F_2$ were selected from the multitude of fragments produced by the abovementioned digestion. They were separated by agarose gel electrophoresis and then extracted and finally cloned by the conventional techniques of molecular biology.

The base material which permitted this isolation, namely the Candida krusei strain is LMCK 31, was isolated from a bronchoalveolar specimen taken from a hospitalized patient. This strain was deposited on Oct. 22, 1993 in the CNCM at the Institut Pasteur, PARIS, under the reference I 1372.

Example 2: Hybridization, By The Deposition Method, of The Probe $F_1$, $F_2$ With Strains of Various Species of Yeasts Hybridization analysis by the deposition method, in accordance with the procedures well known to those skilled in the art, requires immobilizing a previously denatured nucleic acid or population of nucleic acids on a membrane or a filter, such as a positively charged nylon membrane, a nitrocellulose filter or another membrane specially designed for this purpose, which can easily be obtained commercially. The DNA or RNA can easily be immobilized on such membranes or filters and can then be probed or tested for hybridization under multiple stringency conditions with nucleotide sequences or probes in question. Under stringent conditions, the probes whose nucleotide sequences possess the greatest complementary with the target show a greater hybridization level than the probes whose sequences have fewer homologies (are less complementary). The probe $F_1$, $F_2$ of the present invention is tested by hybridization using the deposition method. Thus 6 to 1.5 µg of target total DNA of the test strains listed in Table 1 below, purified by phenol extraction, are denatured (100° C., 5 min) and deposited on a positively charged nylon membrane (Appligène, Illkirch, France) with a MilliBlot apparatus (Millipore Corporation, Bedford, Ma.). The membrane is prehybridized for 2 hours at a temperature of 41.5° C. in ECL buffer (40 ml), in the presence of 5% (w/v) of a blocker (Amersham, Les Ulis, France) and at an NaCl concentration of 0.42 M. A quantity of 600 ng of the probe $F_1$, $F_2$, consisting of equal parts of the two fragments of about 5.6 and 5.4 kb derived from restriction of the total DNA of LMCK 31 by EcoRl, is labeled with peroxidase (ECL system) (Amersham, Les Ulis, France). The probe is added to the reaction medium and hybridization of the probe with the target DNA is carried out for 6 to 18 hours at a temperature of 41.5° C. in ECL buffer (40 ml), in the presence of 5% (w/v) of a blocker (Amersham, Les Ulis, France) and at an NaCl concentration of 0.42 M. The unhybridized probe is removed by two successive washes for 15 min at 41.5° C. with solution 1 (urea 6 M, sodium dodecylsulfate 0.4% (w/v), 20×SSC 2.5% (v/v)) over 5 to 20 min, followed by two successive washes at room temperature with solution 2 (2×SSC) over 5 to 20 min. The membrane is then immersed for 1 min in a mixture of equal volumes of developing reagents 1 and 2 [ECL system (Amersham, Les Ulis, France)], after which it is covered with a Hyperfilm-ECL photographic film for 5 to 30 min, in accordance with the manufacturer's recommendations. A hybridization signal very much stronger than the background is observed only with the DNA of C. krusei or I. orientalis. A complementary assay was able to show that quantities of 15 µg of target genomic DNA belonging to the different species of Candida krusei mentioned in Table 1 do not make it possible to obtain a hybridization signal stronger than that of the control: 1.5 µg of C. krusei.

Example 3: Hybridization, By The Southern Method, of The Probe $F_1$, $F_2$ With EcoRi or HinfI Restriction Fragments of Different Strains of Candida krusei and Different Strains of Various Species The Southern transfer method is an essential technique in molecular biology and comprises the following steps:

the total (genomic) DNA of the strains to be studied is digested by a restriction enzyme and the resulting restriction fragments are separated according to their size by electrophoresis on an agarose gel (0.8% w/v);

the separated DNA is denatured in the gel with sodium hydroxide solution and then neutralized in Tris buffer;

the DNA is transferred from the gel to the filter or positively charged nylon membrane by aspiration under vacuum (vacugène system, Appligène), in a high salt concentration;

the DNA transferred in this way is fixed to the filter by baking at 80° C. for 20 min;

the filter to which the DNA is fixed is subsequently prehybridized in a special buffer which saturates the non-specific binding sites with a carrier DNA or synthetic polymers, and is then hybridized in the hybridization buffer containing the denatured probe, which can be radioactively labeled (hot labeling) or non-radioactively labeled (cold labeling), for example by the fixing of an enzyme such as peroxidase.

The hybridization temperature and conditions are determined so as to allow adequate probe-target hybridization.

Following hybridization, the residual probe which is not specifically hybridized and fixed to the filter is removed by a series of washes, which do not detach the probe fixed specifically to the target.

The probe $F_1$, $F_2$ of the present invention is tested by hybridization using the Southern method. 25 to 5 μg of target total DNA, purified by phenol extraction, are digested by a restriction enzyme under the conditions recommended by the manufacturer (Appligène). The restriction fragments are separated by electrophoresis in 0.8% agarose gel in Tris-Borate-EDTA (TBE) buffer 1×, at 2 V/cm, for 18 h.

After electrophoresis, the separated fragments are transferred to a positively charged nylon membrane (Appligène) by the conventional techniques of alkaline transfer. After fixing of the DNA by baking of the transfer membrane at 80° C. for 20 min, said membrane serves as a support for the hybridizations.

The membrane is incubated for 2 h at 41.5° C. in 40 ml of a prehybridization solution consisting of ECL buffer (Amersham) containing 5% (w/v) of a blocker (Amersham) and 0.42 M NaCl. The incubations take place in a tube in an agitating hybridization oven rotating at 20 to 50 rpm.

After prehybridization, 600 ng of the probe CK1,2, labeled with peroxidase using the ECL system (Amersham, Les Ulis, France) according to the manufacturer's recommendations, are added to the reaction medium. Hybridization is carried out for 18 h at 41.5° C. with agitation at between 20 and 50 rpm. The unhybridized fraction of the probe is subsequently removed by two successive washes with solution 1 [urea 6 M, sodium dodecylsulfate 0.4% (w/v), 20×SSC 2.5% (v/v)] over 5 to 20 min, followed by two successive washes at room temperature with solution 2 (2×SSC) over 5 to 20 min. The membrane is then immersed for 1 min in a mixture of equal volumes of developing reagents 1 and 2 [ECI, system (Amersham, Les Ulis, France)], drained, wrapped in "saran-wrap" and then covered with a Hyperfilm-ECL photographic film for 5 to 30 min, according to the manufacturer's recommendations.

The following were used in the assays corresponding to the hybridization profile of FIG. 1:

a reference standard for the number of nucleotides obtained by HindIII restriction of the total DNA of phage lambda;

a first assay in which the target is formed by the EcoRI restriction fragments of the total DNA of DNA of *Candida krusei* LMCK 31;

a second assay in which the target is formed by the EcoRI restriction fragments of the total DNA of HinfI.

In FIG. 1, the solid lines c nd to the fragments hybridizing with $F_1$, $F_2$. The broken line are the major restriction fragments which are readily observable directly on the restriction profiles. The sizes of the fragments are expressed in kilobases.

Figure 2:
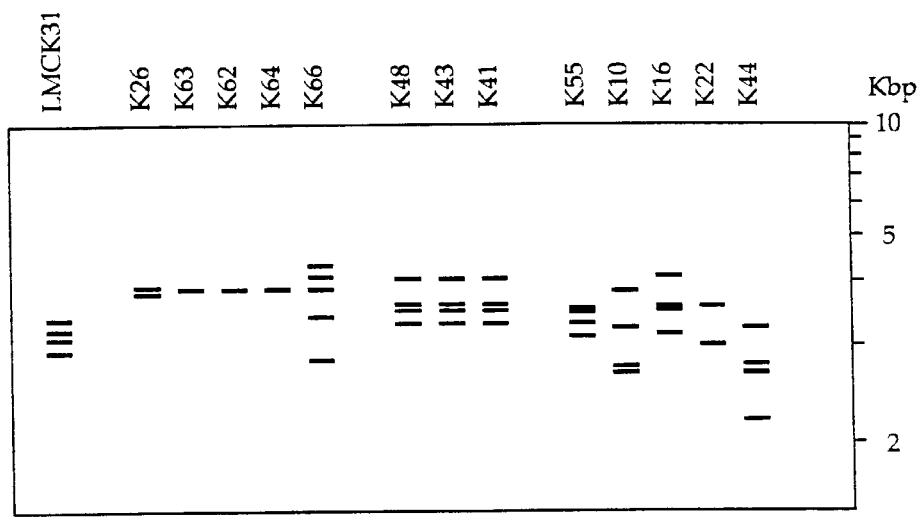
FIG. 2, which shows a hybridization profile, according to the Southern method, of the probe $F_1$, $F_2$ with various strains of Candida krusei.

HinfI restriction fragments of the total DNA of the following different strains of *Candida krusei* were used in the assays corresponding to the hybridization profiles of FIG. 2: LMCK 31, K26, K63, K62, K64, K66, K48, K43, K41, K55, K10, K16, K22 and K44. The strains K62, K63 and K64 originate from the same patient. The same applies to the K41, K43 and K48. Each band represents a fragment hybridizing with $F_1$, $F_2$.

This shows that it is possible to type the different strains within the species *Candida krusei* using one of the probes according to the invention, since the latter clearly reveals the polymorphism in the size of the restriction fragments of the DNA of these strains of *Candida krusei*.

Figures 3A, 3B:
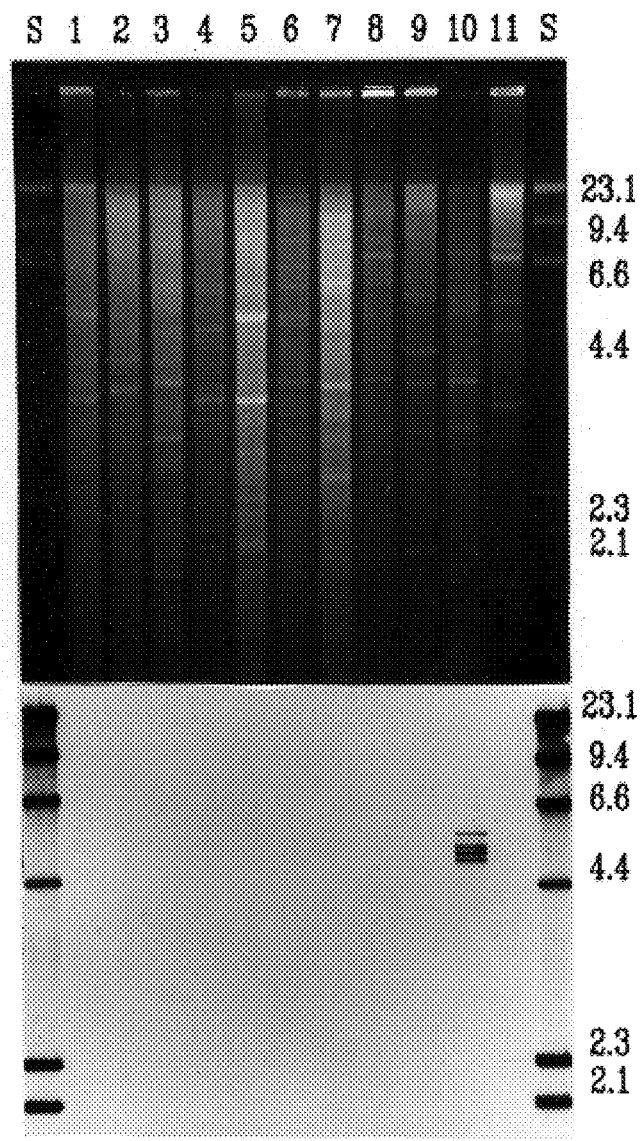
FIG. 3a, which is a photograph of an agarose gel electrophoresis separation of fragments of total DNA obtained by the digestion of different Candida species by EcoRI.
FIG. 3b, which shows a hybridization profile, according to the Southern method under vacuum, of the strains of FIG. 3a with the probe $F_1$, $F_2$.

The microorganisms in question in the assays corresponding to FIGS. 3a and 3b are as follows:

S: Standard: phage lambda digested by HindIII

1: *Candida tropical* is 1058; 2: *C. parapsliosis* CBS 604T; 3: *C. guillermondii* CBS 6021T; 4: *C. lusitaniae* H 278; 5: *C. kefyr*; 6: *C. albicans* serotype β; 7: *C. albicans* serotype A; 8: *C. albicans* ATCC 2091; 9: *C. valida* CBS 638T; 10: *C. krusei* CBS 573T; 11: *Yarrowia lipolytica* CBS 6124T (cf. legends to Table 1 for CBS, ATCC).

In these assays, the fragments of total DNA (6 to 8 μg), digested by EcoRI, of the abovementioned microorganisms are separated by electrophoresis, photographed (FIG. 3a) and then transferred to a nylon membrane by the Southern method under vacuum and hybridized with the probe $F_1$, $F_2$ under the conditions described above. FIG. 3b shows the hybridization profile obtained.

Example 4: Direct Hybridization of The Colonies

For the rapid screening of clinical or other specimens, it may be useful to perform hybridizations directly on the colonies of yeasts obtained after plating of the specimen on an appropriate culture medium and incubation, for example on Sabouraud's medium incubated at 28° C. for 24 h. It is thus possible to identify a colony of *C. krusei* among several colonies with the aid of specific probes.

The probe $F_1$, $F_2$ is tested under the following conditions: The strains of different species and of *C. krusei* are inoculated punctually on the surface of Sabouraud's medium in a Petri dish by the conventional methods of microbiology. Fifteen to thirty strains are studied simultaneously. After 24 h of incubation at between 30 and 35° C., a blot of the colonies is made by applying a disk of positively charged nylon membrane (positive membrane, Appligène) to the surface of the culture medium in contact with the colonies, under a uniform weight (about 10 to 50 grams). When the disk is completely moist, it was removed from the surface and turned over so that the surface which has taken up the blot of the colonies is facing upwards. The disk is then placed on the surface of a sheet of Whatman paper (Whatman 3MM) saturated with 0.5 M NaOH (sodium hydroxide).

The membrane is then rinsed twice by immersion in 400 ml of 5×SSC with vigorous agitation in order to remove the cellular debris fixed to the surface of the membrane. The disk is then partially dried on Whatman 3MM paper with its top side facing upwards. The disk is then used for the hybridizations under conditions identical to those described above. The disk of membrane is hybridized in 40 ml of ECL buffer, 5% of blocker and 0.42 M NaCl, with 400 ng of the probe $F_1$, $F_2$ which has first been denatured and labeled with peroxidase using the ECL system according to the manufacturer's recommendations. After 18 h of hybridization and successive rinses, the only hybridization signals are recorded at the locations of the C. krusei and I. orientalis colonies on the blot made on the membrane.

The probe $F_1$, $F_2$ can also be used under other hybridization conditions by the conventional methods of molecular biology which are well known to those skilled in the art.

TABLE 1

LIST OF THE STRAINS STUDIED BY HYBRIDIZATIONS WITH THE PROBE $F_1$, $F_2$

| STRAIN | REFERENCE | RESULTS |
|---|---|---|
| Candida albicans | ATCC 2091 | – |
| Candida albicans serotype A | Labo Myco LYON | – |
| Candida albicans serotype B | Labo Myco LYON | – |
| Candida boidinii | 34 F 1 | – |
| Candida famata | Labo Myco LYON | – |
| Candida glabrata | Labo Myco LYON | – |
| Candida guillermondii | CBS 6021T | – |
| Candida humicola | CBS 2839T | – |
| Candida inconspicua | Labo Myco LYON | – |
| Candida kefyr | CBS 607T | – |
| Candida krusei | CBS 573T | + |
| Candida krusei (57 strains) | Labo Myco LYON | + |
| Candida lambica | CBS 1876T | – |
| Candida lusitaniae | Labo Myco LYON | – |
| Candida norvegensis | Labo Myco LYON | – |
| Candida parakrusei | Labo Myco Lyon | – |
| Candida parapsilosis | CBS 604T | – |
| Candida rugosa | SIPHV 823 | – |
| Candida tropicalis | CBS 617T | – |
| Candida valida (2) | CBS 638T | – |
| Candida zeylanoides | IPP 207 | – |
| Cryptococcus neoformans | Labo Myco LYON | – |
| Geotrichum candidum | Labo Myco LYON | – |
| Issatchenkia orientalis | CBS 5147T | + |
| Kluyveromyces bulgaricus | CBS 2762T | – |
| Kluyveromyces dobzhanskii | CBS 2104T | – |
| Kluyveromyces drosophilarum | Labo Myco LYON | – |
| Kluyveromyces fragilis | CBS 297T | – |
| Kluyveromyces lactis | CBS 683T | – |
| Kluyveromyces marxianus | CBS 712T | – |
| Kluyveromyces vanudenii | CBS 4372T | – |
| Kluyveromyces wickerhamii | Phaff | – |
| Rhodotorula glutinis | CBS 20T | – |
| Rhodotorula rubra | CBS 17T | – |
| Saccharomyces cerevisiae | CBS 11711T | – |
| Trichosporon cutaneum | IPP 654 | – |
| Yarrowia lipolytica | CBS 6124T | – |
| Zygosaccharomyces rouxii | Labo Myco LYON | – |
| Aspergillus flavus | Labo Myco LYON | – |
| Nocardia asteroides | IPP 1750-88 | – |
| Rhodococcus equi | Labo Myco LYON | – |
| Staphylococcus aureus | Labo Myco LYON | – |
| Escherichia coli | Labo Myco LYON | – |

CBS = Centraal Bureau Voor Schimmelculture, BAARNS, THE NETHERLANDS,
ATCC = American Type Culture Collection, ROCKVILLE, USA,
IPP = Institut Pasteur, PARIS, FRANCE,
Labo Myco LYON = Laboratoire de Mycologie, Faculté de Pharmacie, Université Claude Bernard LYON 1, 8, avenue Rockefeller, 69373 LYON, FRANCE.

What is claimed is:

1. A probe which specifically hybridizes with the DNA and/or RNA of Candida krusei, said probe comprising:
    a) at least one 4 kb to 7 kb EcoRI fragment ($F_1$ or $F_2$) of the Candida krusei strain LMCDK31 or a fragment thereof which retains said specificity;
    b) an analog (Fa) of $F_1$ or $F_2$, or a fragment thereof which retains said specificity; wherein an analog of $F_1$ or $F_2$, is a nucleic acid comprising a nucleotide sequence which differs from $F_1$ or $F_2$, or a fragment thereof, because of the degeneracy of the genetic code;
    c) a complementary strand (Fc) of $F_1$, $F_2$, or Fa, or a fragment thereof which retains said specificity; or
    d) a transcription product of $F_1$, $F_2$, Fa or Fc, or a fragment thereof which retains said specificity;
with the proviso that said probe does not code for ribosomal RNA.

2. A probe according to claim 1 characterized in that at least one EcoRI fragment has a size of between 6.6 to 4.4 kb.

3. A probe according to claim 1 characterized in that said at least one EcoRI fragment has a size of between about 5.6 to 5.4 kb.

4. A single stranded oligonucleotide comprising either RNA or DNA which is fully complementary to one strand of the EcoRI fragment of claim 1.

5. A single stranded oligonucleotide comprising either RNA or DNA which is fully complementary to one strand of the EcoRI fragment of claim 2.

6. A single stranded oligonucleotide comprising either RNA or DNA which is fully complementary to one strand of the EcoRI fragment of claim 3.

7. A method for the specific detection of yeast of the species Candida krusei, characterized in that it comprises using at least one probe according to claim 2.

8. A method for the specific detection of yeast of the species Candida krusei, characterized in that it comprises using at least one probe according to claim 3.

9. A method for the specific detection of yeast of the species Candida krusei, characterized in that it comprises using at least one probe according to claim 4.

10. The probe of claim 1 capable of hybridizing with EcoRI DNA fragments which have a size between 4.4 kb–6.6 kb, said fragments coming from a particular reference strain which is C. krusei CBS 573 T having accession number ATCC6258, under hybridization conditions used in a process for hybridizing a probe with target DNA, said process comprising incubating a membrane having said target DNA fixed thereon; inoculating said membrane for two hours at 41.5° C. in 40 ml of prehybridization solution consisting of ECL buffer containing 5% (w/v) of a blocker and 0.42 M NaCl wherein said incubation takes place in a tube within an agitating hybridization oven rotating at 20–50 rpm; adding 600 ng of the probe CK1, 2 to the solution, said probe being labelled with peroxidase; and carrying out hybridization for 18 hours at 41.5° C. with agitation from 20–50 rpm.

11. The probe of claim 1 wherein said probe is infraspecific.

12. A probe according to claim 1 characterized in that at least one of the fragments $F_1$ and $F_2$ is capable of hybridizing with at least one of the fragments derived from digestion of the total DNA of the Candida krusei strain LMCK 31 by the restriction enzyme HinfI, the size of which is between 7.0 and 2.0 kb.

13. A probe according to claim 1 characterized in that at least one of the fragments $F_1$ and $F_2$ is capable of hybridizing with at least one of the fragments derived from digestion of the total DNA of the Candida krusei strain LMCK 31 by the restriction enzyme HinfI, the size of which is between 3.8 and 2.5 kb.

14. A probe according to claim 1 characterized in that it contains two fragments $F_1$ and $F_2$, which are present in a proportion $F_1/F_2$ of 99/1 to 1/99.

15. A probe according to claim 1 characterized in that it contains two fragments $F_1$ and $F_2$, which are present in a proportion $F_1/F_2$ of 80/20 to 20/80.

16. A probe according to claim 1 characterized in that it contains two fragments $F_1$ and $F_2$, which are present in a proportion $F_1/F_2$ of about 50/50.

17. A probe according to claim 1 characterized in that it is provided with at least one labeling means.

18. A probe according to claim 1 characterized in that the *Candida krusei* strain LMCK 31 is the one deposited in the CNCM at the Institut Pasteur on Oct. 22, 1993 under the number I 1372.

19. A method for the specific detection of yeast of the species *Candida krusei*, characterized in that it comprises using at least one probe according to claim 1.

20. A method according to claim 19 characterized in that:

the total genomic DNA is extracted from the strains to be studied, this total DNA is optionally subjected to enzymatic digestion by at least one restriction enzyme, the optionally digested, total DNA is denatured, the now denatured, total DNA is brought into contact with the probe in order to effect hybridization, wherein said probe has previously been denatured and provided with at least one labeling means, removing unhybridized probe detecting hybridization whereby the detection of a hybridization signal is indicative of the specific detection of yeast of the species *Candida krusei*.

21. In a method of polymerization chain reaction (PCR), wherein the improvement comprises using the probe according to claim 1.

22. A method for differentiation between strains within the species *Candida krusei* using a probe according to claim 1 to differentiate between the strains.

* * * * *

UNITED STATES PATENT AND TRADEMARK OFFICE
CERTIFICATE OF CORRECTION

PATENT NO.    : 5,955,267
DATED         : September 21, 1999
INVENTOR(S)   : Arnaud Carlotti and Jean Villard It is certified that error appears in the above-identified patent and that said Letters Patent is hereby corrected as shown below:

<u>Title page,</u>
Item [22], the phrase "PCT filed: September 7, 1993" should read
-- PCT filed October 27, 1994 --

Item [86], the PCT application "PCT/GB 94/01 931" should read -- PCT/FR 94/01 250 --.

Signed and Sealed this

Twenty-sixth Day of March, 2002

Attest:

*Attesting Officer*

JAMES E. ROGAN
*Director of the United States Patent and Trademark Office*